US008992999B2

(12) United States Patent
Duffy et al.

(10) Patent No.: US 8,992,999 B2
(45) Date of Patent: Mar. 31, 2015

(54) METHODS AND COMPOSITIONS FOR CONTROLLING PARASITIC INFECTIONS OF ANIMALS

(75) Inventors: Cepta Duffy, Ongar Green (IE); Aidan Joseph Connolly, Terenure (IE)

(73) Assignee: Alltech, Inc., Nicholasville, KY (US)

( * ) Notice: Subject to any disclaimer, the term of this patent is extended or adjusted under 35 U.S.C. 154(b) by 1664 days.

(21) Appl. No.: 11/571,053

(22) PCT Filed: Jul. 21, 2004

(86) PCT No.: PCT/US2004/023478
§ 371 (c)(1),
(2), (4) Date: Dec. 21, 2006

(87) PCT Pub. No.: WO2006/022616
PCT Pub. Date: Mar. 2, 2006

(65) Prior Publication Data

US 2008/0008767 A1 Jan. 10, 2008
US 2014/0147515 A2 May 29, 2014

(51) Int. Cl.
*A61K 36/064* (2006.01)
*A61K 33/04* (2006.01)
*A61K 33/02* (2006.01)
*A61K 36/53* (2006.01)
*A61K 31/715* (2006.01)
*A61K 33/30* (2006.01)
*A23K 1/00* (2006.01)
*A23K 1/14* (2006.01)
*A23K 1/16* (2006.01)
*A23K 1/18* (2006.01)
*A61K 36/896* (2006.01)

(52) U.S. Cl.
CPC .............. *A61K 33/30* (2013.01); *A23K 1/008* (2013.01); *A23K 1/14* (2013.01); *A23K 1/1643* (2013.01); *A23K 1/1826* (2013.01); *A61K 31/715* (2013.01); *A61K 33/04* (2013.01); *A61K 36/064* (2013.01); *A61K 36/53* (2013.01); *A61K 36/896* (2013.01)
USPC ...... 424/643; 424/195.16; 424/702; 424/745; 514/54

(58) Field of Classification Search
None
See application file for complete search history.

(56) References Cited

U.S. PATENT DOCUMENTS

| 3,615,679 | A | * | 10/1971 | Tangel et al. ............. 426/62 |
| 4,356,264 | A | * | 10/1982 | Martin .................... 435/119 |
| 4,643,897 | A | | 2/1987 | Gayral et al. |
| 5,017,562 | A | * | 5/1991 | Holmes et al. ............. 514/26 |
| 5,300,491 | A | * | 4/1994 | Andrews et al. ........... 424/780 |
| 5,597,807 | A | * | 1/1997 | Estrada et al. ............. 514/26 |
| 5,739,118 | A | * | 4/1998 | Carrano et al. ............ 514/44 R |
| 5,955,086 | A | | 9/1999 | DeLuca et al. |
| 5,990,178 | A | | 11/1999 | Ninkov |
| 6,322,825 | B1 | * | 11/2001 | Ninkov ................... 424/745 |
| 6,733,759 | B2 | | 5/2004 | Ivey et al. |
| 2002/0160022 | A1 | * | 10/2002 | Schasteen et al. ......... 424/269.1 |
| 2003/0091589 | A1 | * | 5/2003 | Dawson et al. ........... 424/195.16 |
| 2004/0052905 | A1 | * | 3/2004 | Pelletier et al. ............ 426/74 |
| 2005/0058671 | A1 | | 3/2005 | Bedding et al. |
| 2006/0003022 | A1 | * | 1/2006 | McNeff et al. ............ 424/661 |
| 2009/0263416 | A1 | | 10/2009 | Dawson et al. |

FOREIGN PATENT DOCUMENTS

| CN | 1043428 A | 10/1989 |
| EP | 0 828 502 | 12/2001 |
| JP | 61 118189 | 6/1986 |
| JP | 04 278070 | 10/1992 |
| JP | 09-187229 | 7/1997 |
| WO | WO 98/26787 | 6/1998 |
| WO | WO 02/085415 | 10/2002 |
| WO | WO 03/011310 | 2/2003 |
| WO | WO 2007/149437 | 12/2007 |

OTHER PUBLICATIONS

"Report of the Scientific Committee for Animal Nutrition on the Use of Narasin in Feedstuffs for Chickens" from the Opinion of the Scientific Committee for Animal Nutrition expressed on Apr. 14, 1982, pp. 41-45.*
Elliott et al. (Analyst. Jun. 1998; 123 (45R-56R).*
Amon et al. (Bioresource Technology. 1997; 61: 229-237).*
Cheeke (Proceedings of the American Society of Animal Science. 1999: 1-10).*
V.G. Stanley et al., "An Alternative to Antibiotic-Based Drugs in Feed for Enhancing Performance of Broilers Grown on *Eimeria* spp.-Infected Litter," 2004 Poultry Science Association, Inc., Apr. 4, 2003, pp. 39-44.
I. Giannesnans et al. Aristotle University, "Moore Tang Palatability Information Sheet," Clinical Trial Summary, Oregano Extract-Effect on Coccidiosis in Broilers, OH 016, 2003.
Lucio Nisoli, "Report on final results of trila conducted on ROPADIAR . . . ," Nov. 16, 2000, pp. 1-3.
"Case Report of ROPADIAR Powder 10%: egg Production in Layer 08-09," pp. 1-4, 2001.
Institute for Animal Physiology & Animal Feeding Goettingen, Dr. H Bossow, "MooreTang Palatability," Information sheet Oregano Extract-Effect on Coccidiosis, OH 001, Feb. 2002.
Institute for Animal Physiology & Animal Feeding Goettingen, Dr. H Bossow, "MooreTang Palatability," Information sheet Oregano Extract-Effect on *E.coli* and *Aspergillus fumigatus* in Chickens, OH 002. 1997.

(Continued)

*Primary Examiner* — Shanon A Foley
(74) *Attorney, Agent, or Firm* — Valeria L. Calloway; Kilyk & Bowersox P.L.L.C.

(57) ABSTRACT

A composition for preventing or reducing harmful effects of protozoal infection is provided, comprising in one embodiment a yeast cell wall and a preparation derived from oregano. The composition may further include a mineral nutrient selected from selenium and/or zinc. The composition may also include a preparation derived from Yucca. Efficacy of the composition is shown against a variety of protozoal organisms.

19 Claims, No Drawings

(56) References Cited

OTHER PUBLICATIONS

Dr. Thomas Redmann, "Experience with the use of ROPADIAR against histomoniasis in Turkeys," Inst. for Poultry Disease, Justus-Liebig-University Geissen, Jun. 10, 1997, 1 page.

M. Daley et al., "An Alternative Strategy for In-Feed Control of Coccidiosis," 2004 Alltech, Inc. Symposium, Lexington, Kentucky, Poster Presentation, May 23-26, 2004.

N. Aligiannis et al., "Composition and Antimicrobial Activity of the Essential Oils of Two Origanum Species," J. Agric. Food Chem. 2001, 49, 4168-4170.

N.A. Botsglou et al., "Effect of Dietary Oregano Essential Oil on Performance of Chickens and on Iron-Induced Lipid Oxidation of Breast, Thigh and Abdominal Fat Tissues," British Poultry Science, 43: 223-230, 2002.

I. Giannenas et al., "Effect of Dietary Supplementation with Oregano Essential Oil on Performance of Broilers after Experimentational Infection with *Eimeria tenella*," Archives of Animal Nutrition, 2003. vol. 57 (2), p. 99-106.

R. J. W. Lambert et al., "A Study of the Minimum Inhibitory Concentration and Mode of Action of Oregano Essential Oil, Thymol and Carvacrol," Journal of Applied Microbiology, 2001 vol. 91, p. 453-462.

A. Sivropoulou et al., "Antimicrobial and Cytotoxic Activities of Origanum Essential Oils," Journal of Agrc. Food Chem., 1996, vol. 44 p. 1202-1205.

L. Waldenstedt, "Effect of Vaccination Against Coccidiosis in Combination with an Antibacterial Oregano(*Origanum vulgare*) Compound in Organic Broiler Production," Acta. Agric. Scand., Animal Science, 2003. vol. 53 p. 101-109.

R.J. Wallace et al., "Influence of *Yucca shidigera* Extract on Ruminal Ammonia Concentrations and Ruminal Microorganisms," Applied and Environmental Microbiology, Jun. 1994, p. 1762-1767, XP-002444985.

European Patent Application No. EP 07 80 9671 Supplementary European Search Report Apr. 27, 2010.

Obaseiki-Ebor, E.E. "Rifampicin curing of plasmids in *Escherichia coli* K12-rifampicin resistant host" The Journal of Pharmacy and Pharmacology, Jul. 1984, vol. 36, No. 7, pp. 467-470.

J.T. Trevors "Plasmid curing in bacteria" FEMS Microbiology Reviews, Apr. 1, 1986, vol. 32, No. 3-4, pp. 149-157.

Dawson, K.A. et al. "Effects of a Yeast Cell Wall Preparation on Coccidiosis in Broiler Chicks" Poultry Science, vol. 81, No. Supp. 01, Jan. 14, 2002, p. 134.

Spring, P. et al. "The effects of dietary mannanoligosaccharides on cecal parameters and the concentrations of enteric bacteria in the ceca of *Salmonella*-challenged broiler chicks" Poultry Science, vol. 79, No. 2, Feb. 2000, pp. 205-211.

European Patent Application No. EP 04 75 7179 Supplementary European Search Report Aug. 22, 2007.

Database WPI Week Thompson AN 1997-419358 [39] Derwent Publications, Ltd. London, GB.

European Patent Application No. EP 04 75 7179.9 Communication Pursuant to Article 94(3) EPC Jan. 18, 2008.

PCT Application No. PCT/US07/14281 International Search Report Nov. 14, 2007.

Ruiming Lou "Dietary mannan-oligosaccharide as an approach for altering prevalence of antibiotic resistance and distribution of tetracycline resistance determinants in fecal bacteria from swine"; dissertation submitted for the degree of Doctor of Philosophy, University of Kentucky, Lexington, Kentucky, 1995, Chapter 5.

\* cited by examiner

METHODS AND COMPOSITIONS FOR CONTROLLING PARASITIC INFECTIONS OF ANIMALS

TECHNICAL FIELD

This invention relates broadly to novel compositions and methods for controlling parasitic diseases of animals. In particular, the invention relates to compositions and methods for controlling protozoal parasitic infections of animals. Still further, the invention relates to compositions and methods for reducing the harmful effects of protozoal parasitic infections in animals.

BACKGROUND OF THE INVENTION

Protozoal parasitic infections of food species including mammals and birds are characterized by varying degrees of enteritis that results in decreased production and performance. In extreme cases, increased mortality is seen. However, even in less severe infections, losses in feed conversion efficiency and decreased weight gains may represent the difference between profit and loss in modern, intensive animal production situations. For example, coccidial infections are known to be a predisposing factor to other syndromes, in particular necrotic enteritis (a bacterial infection of the intestinal lining resulting in necrosis of the intestinal lining in various regions of the gut). Other protozoans, such as *Histomonas* and *Cochlosoma*, also lead to necrotic enteritis and increased mortality in severe cases, or in less severe cases poor feed utilization, stunted growth, and overall poor performance. The economic effects on producers can be catastrophic. It is standard poultry industry practice to reuse litter. However, such reused litter may serve as a protozoal reservoir for future infections.

Conventional disinfectants are relatively ineffective against protozoans. Thus, thorough cleaning of housing and strict biosecurity measures are necessary to maintain proper hygiene standards and reduce animal exposure. Unfortunately, due to relatively rapid turnaround of hosts (for example, the rapid replacement of flocks in broiler operations), a permanent reservoir of protozoal organisms is often maintained. Even a few organisms are capable of massive multiplication in a few weeks time. Accordingly, control measures beyond maintenance of proper hygiene are required.

Currently known methods of protozoal control include use of anti-protozoal medication. Anti-protozoal drugs are generally effective for their intended purpose, and advantageously may be provided in the feed or via the drinking water to animals being treated. However, a significant disadvantage of current drugs used for treatment/control of protozoa is that, over time, treated organisms may become resistant to particular drugs. Accordingly, different drugs must be used, often in rotation or in a staggered schedule (shuttle programs), to prevent development of resistant organisms. Even in cases where shuttle programs are implemented, it is possible that efficacy against protozoal infections will be compromised during the period when drugs are altered. Additionally, certain drugs, while useful in the control of protozoa, require a predetermined withdrawal period prior to slaughter to allow sale of meat, milk, eggs, etc. from treated animals.

There thus remains a need in the art for alternative methods for controlling protozoal infections in animals and birds. There is further a need in the art for alternative methods for controlling protozoa which do not risk creating resistant organisms.

SUMMARY OF THE INVENTION

In accordance with the purposes of the present invention as described herein, in one aspect of the present invention compositions are provided for preventing or reducing harmful effects of a protozoal infection in an animal suffering from or exposed to a protozoal organism, the composition comprising a yeast cell wall and a preparation derived from oregano. The compositions of the present invention are effective against a variety of protozoal infections, including those caused by protozoal organism selected from *Eimeria* species, *Histomonas* species, *Cochlosoma* species, *Hexamita* species, and combinations thereof. The compositions may be formulated for admixing with food, or may be provided as a dietary supplement. The oregano preparation may be derived by any means known in the art. In one embodiment, the oregano preparation comprises at least one oil derived from oregano by steam distillation.

The compositions may comprise at least one yeast-derived mannanoligosaccharide, wherein the mannanoligosaccharide-containing composition is formulated for feeding to any animal, including bovine, porcine, avian, equine, ovine, lapine, caprine, and aquatic species. The composition may be formulated for feeding to avian species such as a chicken, turkey, duck, goose, pheasant, quail or a companion bird. The yeast may be *Saccharomyces, Candida, Kluyveromyces* and *Torulaspora*, or any combination thereof. In one embodiment of the present invention, the yeast is derived from *Saccharomyces cerevisiae*. Typically, the yeast is derived from *Saccharomyces cerevisiae* strain NCYC 1026. The compositions may comprise dried cells of yeast.

The compositions of the present invention may further comprise at least one mineral nutrient. The mineral nutrient may be selected from at least one of selenium or zinc. Still further, the compositions may comprise a preparation derived from a Yucca plant. The Yucca plant preparation may be derived by chopping, crushing, macerating, pressing, or grinding the Yucca plant to obtain an extract.

In another aspect of the present invention, compositions are provided for preventing or reducing harmful effects of a protozoal infection in an animal, the compositions comprising a yeast cell wall, at least one preparation derived from oregano, and at least one plant preparation derived from Yucca. The yeast cell wall, oregano preparation, and Yucca plant preparation are substantially as described above. The composition may further comprise at least one mineral nutrient, selected from at least one of selenium or zinc. As described above, the compositions may be formulated for admixing with a food, or for feeding as a dietary supplement.

In yet another aspect of the invention, a method for preventing or reducing harmful effects of a protozoal infection in an animal suffering from or exposed to a protozoal organism is provided, comprising administering a composition to the animal comprising a yeast cell wall and a preparation derived from oregano in an amount effective to prevent or reduce protozoal infection or cecal or liver lesions caused by protozoal infection. The compositions may be formulated for admixing with a food, or for feeding as a dietary supplement.

In still yet another aspect of the invention, a method for preventing or reducing harmful effects of a protozoal infection in an animal is provided, comprising administering a composition to the animal comprising a yeast cell wall, at least one preparation derived from oregano, and at least one plant preparation derived from Yucca in an amount effective to prevent or reduce protozoal infection or cecal lesions caused by protozoal infection.

As should be appreciated, the embodiments shown and described are an illustration of one of the modes best suited to carry out the invention. It will be realized that the invention is capable of modification in various, obvious aspects all without departing from the invention. Accordingly, the descriptions and examples provided herein will be regarded as illustrative in nature, and not as restrictive.

DETAILED DESCRIPTION OF THE INVENTION

As discussed above, it is desirable to provide compositions and methods for controlling protozoal parasitic infections in animals which are not drug-based, such as medicated feeds. To achieve this goal, and in accordance with the purposes of the present invention as described herein, novel compositions and methods for controlling protozoal parasitic infections are provided. In particular, the present invention provides novel compositions for controlling protozoal parasitic infections, comprising a yeast cell wall and a preparation derived from oregano. In one embodiment, the yeast cell wall includes at least one mannanoligosaccharide, and the oregano preparation is an oil. The compositions of this invention as described herein may be fed as supplements, or may be incorporated into commercially available foodstuffs. One of skill in the art will appreciate that the amounts of the composition fed will vary depending upon the animal species, the size of the animal, and the type of foodstuff to which the composition is added. The methods of the invention as described herein are suitable for preventing or reducing the harmful effects of protozoal parasitic infections in animals, including but not limited to, bovine, porcine, avian, equine, ovine, lapine, caprine, and aquatic species.

Typically, the yeast cell wall is prepared from a yeast organism using known methodology (see, Peppler, H. J. 1979. Production of yeasts and yeast products. Page 157 in: Microbial Technology & Microbial Processes, Vol. 1 (2d Ed.), Academic Press; incorporated herein by reference). Briefly, a yeast organism (typically *S. cerevisiae* strain NCYC 1026) is grown in accordance with common techniques used in food/beverage-related fermentations. Any of a number of common sugar-containing media, such as diluted molasses, may be used to provide a source of sugars for growth of the yeasts. Other suitable media include wood sugars, sulfite waste liquor, and whey. The yeast biomass may then be separated and washed by centrifugation.

After centrifugation, the organism may be lysed by common methods, such as autolysis and/or hydrolysis at room temperature and pressure. A protease such as papain or any of a number of alkaline or neutral proteases may be added during the lysis phase to accelerate solubilization of yeast proteins and prevent agglutination of intracellular components. Following lysis, the resultant yeast cell wall preparation may be washed, such as by centrifugation and resuspension in a wash solution, and concentrated. The concentrated cell wall may be dried by any suitable method, such as drum drying or spray drying, to form a hygroscopic, water-soluble product.

The Yucca preparation may be derived from a Yucca plant by any suitable method for deriving a liquid extract from the plant, such as by chopping, crushing, macerating, pressing, or grinding the Yucca plant and obtaining a liquid extract therefrom. Optionally, the bark of the Yucca may be removed prior to extracting the liquid. The liquid extract may be converted to powder form for storage and/or transport, such as by drying and optionally admixing with a suitable carrier, prior to addition to the compositions of the present invention.

Typically, an organic or chelated trace mineral formulation will be used. In one embodiment of the present invention, the Se component may be provided as an organic Se source (SEL-PLEX; Alltech, Inc., Nicholasville, Ky.) and the Zn component may be provided as BIOPLEX ZN (Alltech, Inc., Nicholasville, Ky.). However, it will be appreciated that any formulation of trace mineral suitable for provision as a food/feed ingredient or supplement may be used in the compositions of the present invention.

The following examples are presented for illustrative purposes only, and are not to be considered restrictive of the scope of the invention as otherwise described herein.

EXAMPLE 1

Anticoccidial efficacy of the compositions of the present invention in poultry was evaluated against a conventional coccidiostat, Salinomycin (60 g/1000 kg of feed). Three dietary treatments were prepared:

1. Dietary treatment 1: yeast cell wall (1 kg/1000 kg feed), Yucca preparation (500 g/1000 kg feed), selenium (0.2 g/1000 kg feed), and zinc (20 g/1000 kg feed), included in feed at 1.9 kilograms/1000 kg feed.
2. Dietary treatment 2: dietary treatment 1 plus 15 g/1000 kg feed of oregano preparation. The oregano preparation was prepared by steam distillation using methods known in the art to provide an oil, and was added to the dietary treatment as 25 g/1000 kg feed of a powder comprising 60% oregano oil on a synthetic silica carrier. Dietary treatment 2 was included in the feed at a rate of 1.925 kilograms/1000 kg feed.
3. Dietary treatment 3: dietary treatment 1 with the Yucca preparation omitted, plus 30 g/ton of oregano preparation as described above, included in feed at a rate of 1.45 kilograms/1000 kg feed.

Day-old Cobb×Cobb poultry having an average starting body weight of 45 g were separated into cages. Each experimental treatment consisted of 8 cages, with 10 birds per cage (n=80 birds per experimental treatment). Experimental treatments were: (a) negative control (no dietary treatment and no coccidial challenge); (b) positive control (no dietary treatment but provided a coccidial challenge as described below); (c) dietary treatment 1 plus coccidial challenge; (d) dietary treatment 2 plus coccidial challenge; (e) dietary treatment 3 plus coccidial challenge; and (f) salinomycin treatment (60 g/1000 kg feed) plus coccidial challenge.

A coccidial inoculum was prepared, consisting of a mixed species culture of oocysts of *Eimeria acervulina* (60,000 oocysts), *E. maxima* (10,000 oocysts), and *E. tenella* (50,000 oocysts). The inoculum was delivered to birds receiving a coccidial challenge by oral gavage in a volume of 1 ml per bird in water.

On day 0 of the experiment, birds were weighed by cage and allocated to experimental treatments, and feed issued. After an acclimation period (day 14 of the experiment) the birds were weighed by cage and inoculated with the mixed coccidial infection. On day 20 of the experiment, birds were weighed by cage, and feed remaining was weighed. The birds were sacrificed, all bird intestinal lesions were scored, and litter oocysts counted.

Table 1 summarizes the effect of the present invention on live weight gain and feed conversion. The compositions of the invention (dietary treatments 2 and 3) provided significant increases in weight gain in inoculated birds, compared to nontreated and inoculated controls. There was no statistically significant effect on feed conversion.

TABLE 1

The effect of treatments on average live weight gains (kg) and feed conversion ratios in chicks challenged with an *Eimeria* challenge[#].

| Treatment | Challenge | Avg Live Wt gain Day 14-20 | Weight Day 0-20 | Feed Conversion ratio Day 14-20 | Feed Conversion ratio Day 0-20 |
|---|---|---|---|---|---|
| a | No  | $.318^a$   | $.572^a$    | $1.444^a$    | $1.573^a$ |
| b | Yes | $.200^c$   | $.463^b$    | $1.995^b$    | $1.839^b$ |
| c | Yes | $.214^{cd}$| $.462^b$    | $1.860^b$    | $1.827^b$ |
| d | Yes | $.225^{de}$| $.491^{bcd}$| $1.847^b$    | $1.798^b$ |
| e | Yes | $.235^e$   | $.474^{bcd}$| $1.672^c$    | $1.748^{bc}$ |
| f | Yes | $.266^b$   | $.522^c$    | $1.568^{ac}$ | $1.653^{ac}$ | n = 8 groups of 10 birds for each treatment.
[#]= Different subscripts within a column denote treatment differences, ($p < 0.05$), as determined by Analysis of Variance and Tukey's pairwise Post Hoc analysis.

Similarly, the compositions of the present invention reduced the severity of intestinal lesions (Table 2) compared to nonmedicated, challenged groups. Lesion scores were observed and recorded according to the system of Johnson and Reid (Johnson, J. K., Reid, W. M. 1970. Anticoccidial drugs: lesion scoring techniques in battery and floor pen experiments with chickens. Exp. Parasitol. 28, 30-36; incorporated herein by reference), wherein 0 is normal and severity of lesions is ranked from 1-4, with 4 representing the most severe infection.

TABLE 2

The effect of treatments on average lesion scores observed in the upper, middle and ceca sections of the intestine in chicks challenged with an *Eimeria* challenge[#].

| Treatment | Challenge | Upper | Middle | Ceca | Average |
|---|---|---|---|---|---|
| a | No  | $0^a$      | $0^a$       | $0^a$       | 0 |
| b | Yes | $2.0^c$    | $1.9^c$     | $2.6^b$     | 2.2 |
| c | Yes | $1.6^b$    | $1.7^{cd}$  | $2.1^{bc}$  | 1.8 |
| d | Yes | $1.5^b$    | $1.5^{ce}$  | $1.9^{dc}$  | 1.6 |
| e | Yes | $1.4^b$    | $1.4^{de}$  | $2.0^{dc}$  | 1.6 |
| f | Yes | $1.4^b$    | $0.8^b$     | $1.6^{dc}$  | 1.3 | n = 8 groups of 10 birds for each treatment.
[#]= Different subscripts within a column denote treatment differences, ($p < 0.05$), as determined by Analysis of Variance and Tukey's pairwise Post Hoc analysis.

None of the dietary treatments had a statistically significant effect on litter oocyst counts (data not shown).

EXAMPLE 2

It was of interest to compare the effects of the compositions of the present invention on a variety of different protozoal parasites. Blackhead is an acute or chronic protozoan disease of fowl, primarily affecting the cecae and liver, caused by *Histomonas meleagridis*. Symptoms include loss of appetite, increased thirst, drowsiness, and diarrhea.

A total of 750 1 day old Hubbard Hi-Y broilers were used in this study. Animals were separated into 5 pens (150 birds per pen, day 0 average weight 40 g/broiler chick). Each pen contained 4 water fountains and 4 22 kg capacity feed tubes. Each pen had 2 inches of new wood shaving bedding top dressed with 1 inch of old bedding from a commercial broiler breeder flock, with the exception of a control pen which had 3 inches of new bedding only. The basal feed was a commercial corn-soy based diet. Starter feed was fed from day 0 to 21 of the experiment, and grower feed was fed from day 22 to 42. Diet 1 and diet 2 from Example 1 above were added to the basal diet as premixes (1.9 kg/ton). The conventional medicated feed premix Histostat (nitarsone, 170.3 g/ton) was added as a positive control. The basal diet composition is presented in Table 3.

TABLE 3

Basal diet composition (lbs).

| INGREDIENT | STARTER | GROWER |
|---|---|---|
| Yellow corn 7.5% | 1081.6 | 1194.0 |
| Soy meal 47.5% | 743.3 | 641.2 |
| AnVeg Fat Blend | 81.7 | 80.0 |
| Limestone fine | 39.2 | 36.1 |
| Salt | 6.0 | 5.0 |
| Choline Cl 60% | 1.5 | 0.9 |
| Trace mineral mix | 1.4 | 0.8 |
| Vitamin premix | 0.8 | 1.0 |
| Biofos | 32.8 | 28.8 |
| Sodium bicarbonate | 6.0 | 6.0 |
| Tribasic Cu Cl | 0.5 | 0.5 |
| L-Lysine HCl | 0.0 | 0.5 |
| DL-Meth 99% | 4.3 | 4.2 |
| Se mix | 1.0 | 1.0 |
| Total | 2000 | 2000 |

To expose the broilers to *H. meleagridis*, litter was collected from a commercial broiler breeder flock and the presence of *Heterakis gallinarum* was verified. *H. gallinarum* (cecal worm) are known to shed *H. meleagridis* in their eggs. On days 7, 8, 9, 10, 11, and 12, contaminated litter was top dressed (approximately 2 pounds/pen/day) in 4 of the 5 pens. The fifth pen was kept as an unchallenged control. The animals were visually inspected daily for general health and response to challenge. After day 7, all animals were observed for clinical signs of infection. On days 28, 35, and 42, 25 randomly selected birds were euthanized, and cecal and liver lesions scored as follows:

Cecal Scores

0—Normal;

1—Slight thickening of cecal wall;

2—Moderately thickened cecal wall or slight/moderate cecal core;

3—Moderate thickening of cecal wall and cecal core;

4—Ceca grossly enlarged due to presence of large cecal core.

Liver Score

0—Normal;

1—Slight mottling of liver;

2—Moderate mottling of liver;

3—Concentrated areas of necrotic liver tissue.

Treatments (by pen) were: (1) non-challenged (with *H. meleagridis*) non-supplemented; (2) challenged but non-supplemented; (3) challenged and provided Histostat; (4) challenged and provided dietary treatment 1 as described in Example 1; and (5) challenged and provided dietary treatment 2 as described in Example 1. Results are presented in Tables 4-9.

TABLE 4

Pen feed consumption (kg).

| Treatment | Day 28 | Day 35 | Day 42 |
|---|---|---|---|
| 1 | 201.9 | 291.7 | 412.7 |
| 2 | 192.4 | 238.1 | 354.7 |
| 3 | 177.6 | 221.4 | 336.8 |
| 4 | 196.5 | 253.2 | 354.3 |
| 5 | 203.8 | 267.4 | 372.0 |

TABLE 5

Average weight/bird (kg).

| Treatment | Day 28 | Day 35 | Day 42 |
|---|---|---|---|
| 1 | 0.871 | 1.362 | 1.709 |
| 2 | 0.768 | 1.183 | 1.612 |
| 3 | 0.786 | 1.334 | 1.860 |
| 4 | 0.874 | 1.326 | 1.871 |
| 5 | 0.870 | 1.221 | 1.683 |

TABLE 6

Feed efficiency.

| Treatment | Day 28 | Day 35 | Day 42 |
|---|---|---|---|
| 1 | 1.622 | 1.854 | 2.547 |
| 2 | 1.884 | 2.101 | 2.697 |
| 3 | 2.150 | 2.066 | 2.717 |
| 4 | 1.772 | 1.902 | 2.152 |
| 5 | 1.662 | 1.906 | 2.125 |

TABLE 7

Mortality (%).

| Treatment | Day 28 | Day 35 | Day 42 |
|---|---|---|---|
| 1 | 0.00 | 3.33 | 8.00 |
| 2 | 6.00 | 16.00 | 16.67 |
| 3 | 24.67 | 26.67 | 26.67 |
| 4 | 10.67 | 13.33 | 13.33 |
| 5 | 1.33 | 3.33 | 3.33 |

TABLE 8

Average cecal lesion scores.

| Treatment | Day 28 | Day 35 | Day 42 |
|---|---|---|---|
| 1 | $0.080^a$ | $0.080^a$ | $0.200^a$ |
| 2 | $1.840^c$ | $1.560^c$ | $1.560^d$ |
| 3 | $1.040^b$ | $0.640^b$ | $0.960^c$ |
| 4 | $0.880^b$ | $0.960^b$ | $0.720^{b,c}$ |
| 5 | $0.760^b$ | $0.640^{b,c}$ | $0.440^{a,b}$ |

TABLE 9

Average liver lesion scores.

| Treatment | Day 28 | Day 35 | Day 42 |
|---|---|---|---|
| 1 | $0.000^a$ | $0.000^a$ | $0.000^a$ |
| 2 | $0.760^b$ | $1.160^c$ | $0840^b$ |
| 3 | $0.000^a$ | $0.000^a$ | $0.040^a$ |
| 4 | $0.040^a$ | $0.320^b$ | $0.080^a$ |
| 5 | $0.040^a$ | $0.240^b$ | $0.000^a$ |

Feed consumption was greatest for the unchallenged group and lowest for the group provided Histostat. Feed efficiency, calculated as feed consumption through a period by weight gained, was greatest in the unchallenged group through days 28 and 35. Feed efficiency was greatest on day 42 in the group provided dietary treatment 2. At each day observed, mortality was lowest in the unchallenged group and in the group provided dietary treatment 2. On day 42, cecal lesions were significantly higher in the group provided Histostat than in the group provided dietary treatment 2. Cecal lesions were less severe in birds provided the composition of the present invention in comparison to the birds receiving Histostat. The results of the present experiment suggest that birds challenged with *H. meleagridis* and provided the compositions of this invention performed in a similar manner as birds provided a commercial medicated feed, and significantly better than untreated challenged birds.

EXAMPLE 3

*Cochlosoma anatis* is a flagellated protozoan parasite of birds, which is considered a primary source of loss performance and mortality in turkeys. The purpose of this experiment was to compare the effects of the compositions of the present invention to conventional treatments for *C. anatis*, specifically Histostat (170.3 g/ton of feed) and monensin (72 g/ton of feed) provided as premixes.

A total of 360 1 day old Hybrid turkey hens were used in this study. Animals were separated into 36 pens (10 birds per pen). With the exception of the unchallenged controls, each pen had 2 inches of new wood shaving bedding top dressed with 1 inch of old bedding from a commercial turkey flock known to have had coccidiosis, to promote industry conditions. The basal feed was a commercial corn-soy based diet (Table 10). Diet 1 and diet 2 from Example 1 above were added to the basal diet as premixes (1.9 kg/ton). All birds and feeds were weighed on days 0, 7, 14, and 21.

TABLE 10

Basal diet composition.

| INGREDIENT | STARTER (%) |
|---|---|
| Corn meal | 41.54 |
| Soy meal | 48.78 |
| AnVeg Fat Blend | 4.09 |
| Limestone | 1.35 |
| Dical 21/18.5% | 3.10 |
| Salt | 0.10 |
| TBCC | 0.03 |
| Choline Cl | 0.15 |
| Vitamin premix | 0.05 |
| Sodium bicarbonate | 0.20 |
| Mineral premix | 0.10 |
| L-Lysine HCl | 0.19 |
| DL-Meth 99% | 0.28 |
| Se mix | 0.05 |

*C. anatis* inoculum was prepared as follows:
1. A frozen isolate was thawed at 37° C.
2. Thawed isolate was suspended in phosphate buffer (10-20 ml).
3. Fifteen one-day-old poults, identified as "first passage" poults, were each orally inoculated with 1.5 ml of the inoculum and placed in clean batter pens for 7 days.
4. On day 7 post-inoculation, the poults were feed fasted for 6 hours, euthanized, and their jejunum and ileum removed.
5. Intestinal mucosa from the euthanized poults was scraped into a collection flask containing phosphate buffer.
6. 30 healthy 7 day old poults ("second passage" poults) were inoculated with 2 ml of the intestinal scraping/buffer mixture and placed in clean battery pens for 7 days.
7. On day 7 post inoculation, the "second passage" poults were feed fasted for 6 hours, euthanized, and their jejunum and ileum removed.
8. Intestinal mucosa from the euthanized "second passage" poults was scraped into a collection flask containing phosphate buffer.

9. The intestinal scrapings were homogenized by repeated passage through a syringe with 20 gauge needle, and the material was coarse filtered through sterile gauze.

10. The number of C. anatis per ml in this second pass material was counted by hemacytometer.

11. The homogenate was then diluted with phosphate buffer such that a 1 ml dose contained approximately $2\times10^6$ C. anatis.

On day 14 of the experimental period, C. anatis was delivered in a 1 ml volume to each poult except those in the unchallenged control group.

On day 21, all birds were weighed and euthanized. The entire intestinal tract was removed and scored on a scale of 0-4 based on severity of lesions as follows:

0—no lesions;

1—slight observations of sloughed/flattened tissue areas within the lumen or of "enteritis like" lesions around the diverticulum;

2—minimal observations of sloughed/flattened tissue areas within the lumen or of "enteritis like" lesions around the diverticulum;

3—moderate observations of sloughed/flattened tissue areas within the lumen or of "enteritis like" lesions around the diverticulum;

4—severe observations of sloughed/flattened tissue areas within the lumen or of "enteritis like" lesions around the diverticulum.

Treatments (by pen) were: (1) non-challenged (with C. anatis) non-supplemented; (2) challenged non-supplemented; (3) challenged and provided Histostat; (4) challenged and provided monensin; (5) challenged and provided dietary treatment 1 from Example 1; and (6) challenged and provided dietary treatment 2 from Example 1. Results are presented in Tables 11-15.

TABLE 11

Average weight gain (g).

| Treatment | Day 7 | Day 14 | Day 21 |
|---|---|---|---|
| 1 | $45.8^b$ | $182.3^a$ | $245.0^a$ |
| 2 | $54.2^{ab}$ | $174.5^{ab}$ | $202.3^b$ |
| 3 | $64.2^a$ | $174.2^{ab}$ | $229.2^a$ |
| 4 | $53.3^{ab}$ | $160.0^b$ | $225.0^a$ |
| 5 | $51.7^{ab}$ | $178.3^{ab}$ | $228.3^a$ |
| 6 | $60.8^{ab}$ | $181.7^a$ | $245.8^a$ |

TABLE 12

Feed Efficiency (Feed intake/Weight gain).

| Treatment | Day 7 | Day 14 | Day 21 | Day 21* |
|---|---|---|---|---|
| 1 | $1.254^b$ | $1.490^a$ | $1.625^a$ | $1.625^a$ |
| 2 | $1.136^{ab}$ | $1.474^{ab}$ | $1.906^a$ | $1.880^b$ |
| 3 | $1.130^a$ | $1.505^{ab}$ | $1.716^a$ | $1.679^a$ |
| 4 | $1.170^{ab}$ | $1.544^b$ | $1.689^a$ | $1.619^a$ |
| 5 | $1.183^{ab}$ | $1.523^{ab}$ | $1.744^a$ | $1.664^a$ |
| 6 | $1.134^{ab}$ | $1.493^a$ | $1.621^a$ | $1.621^a$ |

*Feed efficiency at day 21, adjusted for mortality by adding weight gain of dead to pen weight gain.

TABLE 13

Mortality (%).

| Treatment | Day 7 | Day 14 | Day 21 |
|---|---|---|---|
| 1 | 0.00 | 0.00 | 0.00 |
| 2 | 0.00 | 0.00 | 1.67 |
| 3 | 0.00 | 0.00 | 1.67 |
| 4 | 0.00 | 0.00 | 3.33 |
| 5 | 0.00 | 0.00 | 5.00 |
| 6 | 0.00 | 0.00 | 0.00 |

TABLE 14

Average C. anatis lesion scores.

| Treatment | Day 21 |
|---|---|
| 1 | $0.233^a$ |
| 2 | $2.061^c$ |
| 3 | $1.300^{bc}$ |
| 4 | $1.150^b$ |
| 5 | $1.400^{bc}$ |
| 6 | $1.083^{ab}$ |

As expected, at day 21 the untreated, challenged group had inferior weight gain compared to other groups. Greatest weight gain was seen on day 21 in the turkeys provided diet 2, significantly greater than challenged, untreated birds. The birds provided diet 2 had the fewest C. anatis lesions of any of the groups studied. Accordingly, the compositions of the present invention gave similar results in comparison to conventional medicated preparations for treatment of C. anatis.

It is accordingly shown herein that the present invention provides suitable compositions and methods for control or reduction of harmful effects of various protozoal parasites of animals. The compositions are efficacious, and provide a level of control of protozoal infections comparable to that of conventional drug-based treatments.

The foregoing description of the preferred embodiment of this invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated.

All such modifications and variations are within the scope of the invention as determined by the appended claims when interpreted in accordance with the breadth to which they are fairly, legally, and equitably entitled.

What is claimed is:

1. A composition formulated for oral administration for reducing harmful effects of a protozoal infection in an animal, the composition comprising a yeast cell wall, at least one preparation derived from oregano,and an unfractionated Yucca preparation.

2. The composition of claim 1, wherein the composition comprises at least one yeast-derived mannanoligosaccharide.

3. The composition of claim 2, wherein the mannanoliosaccharide-containing composition is formulated for feeding to bovine, porcine, avian, equine, ovine, lapine, caprine, and aquatic species.

4. The composition of claim 1, wherein the yeast is derived from a species selected from the group consisting of *Saccharomyces, Candida, Kluyveromyces* and *Torulaspora*.

5. The composition of claim 4, wherein the yeast is derived from *Saccharomyces cerevisiae*.

6. The composition of claim 5, wherein the yeast is derived from *Saccharomyces cerevisiae* strain NCYC 1026.

7. The composition of claim 1, wherein the Yucca plant preparation is derived by chopping, crushing, macerating, pressing, or grinding the Yucca plant to obtain an extract.

8. The composition of claim 1, further comprising at least one mineral nutrient.

9. The composition of claim 8, wherein the mineral nutrient comprises at least one of selenium or zinc.

10. The composition of claim 1, wherein the oregano preparation is an oil derived from oregano.

11. The composition of claim 1, whereby the composition is formulated for admixing with a food or animal feed.

12. The composition of claim 1, whereby the composition is formulated for feeding as a dietary supplement.

13. The composition of claim 1, wherein the composition comprises dried cells of yeast.

14. The composition of claim 1, wherein the animal is an avian species.

15. The composition of claim 14, wherein the avian species is a chicken, turkey, duck, goose, pheasant, or quail.

16. The composition of claim 13, wherein the protozoal organism is selected from the group consisting of *Eimeria* species, *Histomonas* species, *Cochlosoma* species, *Hexamita* species, and any combinations thereof.

17. A method for preventing or reducing harmful effects of a protozoal infection in an animal, comprising administering a composition to the animal comprising a yeast cell wall, at least one preparation derived from oregano, and an unfractionated yucca preparation in an amount effective to prevent or reduce protozoal infection or cecal lesions caused by protozoal infection.

18. The method of claim 17, whereby the composition is formulated for admixing with a food or animal feed.

19. The method of claim 17, whereby the composition is formulated for feeding as a dietary supplement.

* * * * *